United States Patent [19]
Hotson et al.

[11] Patent Number: 5,859,024
[45] Date of Patent: Jan. 12, 1999

[54] INSECTICIDAL, ACARICIDAL OR NEMATICIDAL 3-CYANO-8-AZABICYCLO [3.2.1]OCTANE DERIVATIVES

[75] Inventors: Matthew Brian Hotson, Binfield; Roger Salmon, Bracknell, both of United Kingdom

[73] Assignee: Zeneca Limited, London, England

[21] Appl. No.: 855,521

[22] Filed: May 31, 1997

[30] Foreign Application Priority Data

May 13, 1996 [GB] United Kingdom ................... 9609978
Nov. 11, 1996 [GB] United Kingdom ................... 9623437

[51] Int. Cl.[6] ................... C07D 471/08; C07D 453/02; C07D 451/02; C07D 451/14; A61K 31/435; A61K 31/42

[52] U.S. Cl. ................... 514/299; 546/124; 546/125; 546/112

[58] Field of Search ................... 546/124, 125; 514/299

[56] References Cited

U.S. PATENT DOCUMENTS

| Re. 35,593 | 8/1997 | Oriek et al. ................... 546/124 X |
|---|---|---|
| 3,120,537 | 2/1964 | Archer et al. ................... 260/292 |
| 3,133,073 | 5/1964 | Archer ................... 260/292 |
| 3,308,131 | 3/1967 | McKusick ................... 260/294 |
| 3,501,461 | 3/1970 | Newallis et al. ................... 260/239 |
| 3,546,232 | 12/1970 | Kaiser et al. ................... 260/292 |
| 3,556,943 | 1/1971 | Fonken et al. ................... 195/51 |
| 3,657,257 | 4/1972 | Helsley ................... 260/292 |
| 4,180,669 | 12/1979 | Winn ................... 546/240 |
| 4,393,069 | 7/1983 | Langbein et al. ................... 424/265 |
| 4,590,270 | 5/1986 | Kompis et al. ................... 544/320 |
| 4,774,249 | 9/1988 | Kompis et al. ................... 514/272 |
| 5,491,148 | 2/1996 | Berger et al. ................... 514/305 |

FOREIGN PATENT DOCUMENTS

| 0 031 219 | 7/1981 | European Pat. Off. . |
|---|---|---|
| 0 216 625 | 4/1987 | European Pat. Off. . |
| 0 307 142 | 3/1989 | European Pat. Off. . |
| 0 315 390 | 5/1989 | European Pat. Off. . |
| 0 398 578 | 11/1990 | European Pat. Off. . |
| 0 498 331 | 8/1992 | European Pat. Off. . |
| 0 518 805 | 12/1992 | European Pat. Off. . |
| 2 548 666 | 1/1985 | France . |
| 27 49 584 | 5/1978 | Germany . |
| 1 061 472 | 3/1967 | United Kingdom . |
| 1304649 | 1/1973 | United Kingdom . |
| 91/17156 | 11/1991 | WIPO . |
| 92/01688 | 2/1992 | WIPO . |
| 93/00313 | 1/1993 | WIPO . |
| 93/14636 | 8/1993 | WIPO . |
| 93/25527 | 12/1993 | WIPO . |
| 95/03306 | 2/1995 | WIPO . |
| 96/08968 | 3/1996 | WIPO . |
| 96/36637 | 11/1996 | WIPO . |
| 96/37494 | 11/1996 | WIPO . |
| 97/13770 | 4/1997 | WIPO . |
| 97/43286 | 11/1997 | WIPO . |

OTHER PUBLICATIONS

Archer, S., et al., J. Am. Chem. Soc., "The Action of Nucleophilic Agents on 3 α–Chlorotropane," vol. 80, 1958, pp. 4677–4681.

Bell, M.R., et al., J. Am. Chem. Soc., "Ethyl 3α–Phenyltropane–3β–carboxylate and Related Compounds," vol. 82, No. 7–9, 1960, pp. 4638–4641.

(List continued on next page.)

Primary Examiner—Floyd D. Higel
Attorney, Agent, or Firm—Dianne Burkhard

[57] ABSTRACT

The invention provides novel compounds of formula (I) and formula (II)

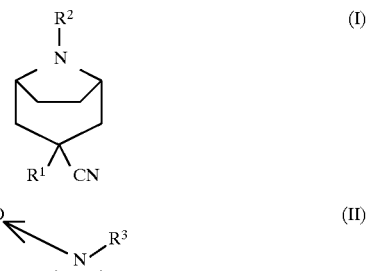

wherein $R^1$ represents a group of formula (A)

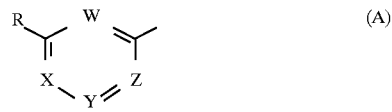

where each of W, X, Y and Z and represents either a group CR or the nitrogen atom, provided that not more than two of W, X, Y and Z represent the nitrogen atom and where each R present is independently selected from hydrogen and halogen atoms and cyano, amino, hydrazino, acylamino, hydroxy, alkyl, hydroxyalkyl, alkoxy, haloalkyl, haloalkoxy, alkenyl, alkenyloxy, alkoxyalkenyl, alkynyl, carboxylic acyl, alkoxycarbonyl, aryl and heterocyclyl groups, said groups comprising up to 6 carbon atoms, and wherein $R^2$ represents a group $XR^3$ where X represents oxygen or a group $NR^4$ where $R^3$ and $R^4$ are individually selected from hydrogen or a group selected from alkyl, aryl, heteroaryl, aralkyl, heteroarylalkyl, alkenyl, aralkenyl, alkynyl, heterocyclylalkyl, alkoxycarbonyl, and carboxylic acyl groups, said groups comprising from 1 to 15 carbon atoms, said groups being optionally substituted with one or more substituents selected from, halogen, cyano, carboxyl, carboxylic acyl, carbamyl, alkoxycarbonyl, alkoxy, alkylenedioxy, hydroxy, nitro, haloalkyl and alkyl groups; and acid addition salts and quaternary ammonium salts and N-oxides derived therefrom.

The compounds have useful insecticidal properties.

8 Claims, No Drawings

OTHER PUBLICATIONS

Cignarella, G., et al., J.Am. Chem. Soc., "A New Synthesis of Tropane Derivatives," vol. 83, No. 10–12, 1961, pp. 4999–5003.

Daum, S. J., ete al., J. Med. Chem., "Analgesic Activity of the Epimeric Tropane Analogs of Meperidine. A Physical and Pharmacological Study," vol. 18, No. 5, 1975, pp. 496–501.

Gutkowska, B., et al., Acta Polon. Pharm., "Syntezy Niektorych Pochodnych 8–Alkilo–8–Aza–Bicyklo[3.2.1] Oktan–3–Onu," vol. 38, No. 4, 1981, pp. 411–415.

Lowe, J. A., et al., J. Med. Chem., "Aza–Tricyclic Substance P Antagonists," vol. 37, No. 18, 1994, pp. 2831–2840.

Maag, H., et al., Helvetica Chimica Acta, "94.5–(N–Arylnortropan–3–yl)– and 5–(N–Arylpiperidin–4–yl)–2,4–diaminopyrimidines. Novel Inhibitors of Dihydrofolate Reductase," vol. 69, No. 4, 1986, pp. 887–897.

Repke, D. B., et al., J. Org. Chem., "Abbreviated Ibogaine Congeners. Synthesis and Reactions of Tropan–3–yl–2– and –3–indoles. Investigation of an Unusual Isomerization of 2–Substituted Indoles Using Computational and Spectroscopic Techniques," vol. 59, No. 8, 1994, pp. 2164–2171.

Zirkle, C. L., et al., J. Org. Chem., "The Isomeric 3–Oxa– and 3–Thiagranatanin–7–ols and Their Derivatives; Reduction of Bicyclic Amino Ketones Related to Tropinone," vol. 26, 1961, pp. 395–407.

INSECTICIDAL, ACARICIDAL OR NEMATICIDAL 3-CYANO-8-AZABICYCLO [3.2.1]OCTANE DERIVATIVES

This invention relates to novel bicyclic amines, to processes for preparing them, to insecticidal compositions comprising and to methods of combatting and controlling insect pests therewith.

The invention provides compounds of formula (I) and formula (II)

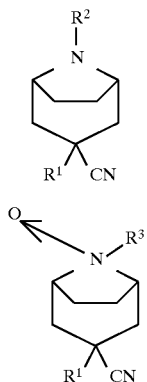

wherein $R^1$ represents a group of formula (A)

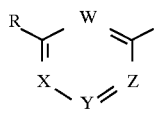

where each of W, X, Y and Z represents either a group CR or the nitrogen atom, provided that not more than two of W, X, Y and Z represent the nitrogen atom and where each R present is independently selected from hydrogen and halogen atoms and cyano, amino, hydrazino, acylamino, hydroxy, alkyl, hydroxyalkyl, alkoxy, haloalkyl, haloalkoxy, alkenyl, alkenyloxy, alkoxyalkenyl, alkynyl, carboxylic acyl, alkoxycarbonyl, aryl and heterocyclyl groups, said groups comprising up to 6 carbon atoms, and wherein $R^2$ represents a group $XR^3$ where X represents oxygen or a group $NR^4$ where $R^3$ and $R^4$ are individually selected from hydrogen or a group selected from alkyl, aryl, heteroaryl, aralkyl, heteroarylalkyl, alkenyl, aralkenyl, alkynyl, heterocyclylalkyl, alkoxycarbonyl, and carboxylic acyl groups, said groups comprising from 1 to 15 carbon atoms, said groups being optionally substituted with one or more substituents selected from, halogen, cyano, carboxyl, carboxylic acyl, carbamyl, alkoxycarbonyl, alkoxy, alkylenedioxy, hydroxy, nitro, haloalkyl and alkyl groups; and acid addition salts and quaternary ammonium salts and N-oxides derived therefrom. $R^1$ is preferably a halo-substituted phenyl, pyridyl or diazinyl group.

In a preferred aspect invention provides compounds of formula (I) and formula (II) where $R^1$ represents an optionally halogen substituted phenyl group or an optionally halogen substituted pyridyl, pyridazinyl or pyrazinyl group and each of $R^3$, and $R^4$ (if present), represents hydrogen or a $C_{1-6}$ alkyl, alkenyl, alkynyl, phenyl, benzyl, pyridylmethyl, thienylmethyl, thiazolylmethyl group which may be optionally substituted with one or more alkyl, alkoxy, alkoxycarbonyl, cyano, optionally substituted alkane sulphonyl groups or halogen atoms; and acid addition salts thereof.

One particularly preferred group of compounds are those wherein $R^1$ represents an optionally halogen substituted phenyl or pyridyl group, X represents oxygen and $R^3$ represents a alkyl group containing up to 4 carbon atoms.

An especially preferred group of compounds are those wherein $R^1$ represents a 5-halopyrid-3-yl group, X represents oxygen and $R^3$ represents alkyl.

Specific compounds of formula I according to the invention include those set out in Table I below in which the groups represented by $R^1$ and $R^2$ are given for each compound.

TABLE I

| No. | $R^1$ | $R^2$ |
|---|---|---|
| 1 | 5-chloropyrid-3-yl | methoxy |
| 2 | 3,5-difluorophenyl | methoxy |
| 3 | 2,3-difluorophenyl | methoxy |
| 4 | pentafluorophenyl | methoxy |
| 5 | 2,3-dichlorophenyl | methoxy |
| 6 | 5-chloropyrid-3-yl | benzyloxy |
| 7 | 4-methoxyphenyl | benzyloxy |
| 8 | phenyl | benzyloxy |
| 9 | 3,5-difluorophenyl | hydroxy |
| 10 | 3,5-difluorophenyl | benzyloxy |
| 11 | 3,5-difluorophenyl | dimethylamino |
| 12 | 3,5-difluorophenyl | phenylamino |
| 13 | 3,5-difluorophenyl | 3-methylbenzylamino |
| 14 | 3,5-difluorophenyl | 4-chlorobenzyloxy |
| 15 | 5-bromopyrid-3-yl | methoxy |
| 16 | 5-chloropyrid-3-yl | allyloxy |
| 17 | 5-chloropyrid-3-yl | propargyloxy |
| 18 | 5-chloropyrid-3-yl | dimethylamino |
| 19 | 5-chloropyrid-3-yl | phenylamino |
| 20 | 5-chloropyrid-3-yl | amino |
| 21 | 5-chloropyrid-3-yl | hydroxy |
| 22 | 5-chloropyrid-3-yl | t-butoxycarbonylamino |
| 23 | 5-chloropyrid-3-yl | 2,2-difluoroethoxy |
| 24 | 5-chloropyrid-3-yl | 2-methylpropoxy |
| 25 | 5-chloropyrid-3-yl | acetoxy |
| 26 | 5-chloropyrid-3-yl | acetylamino |
| 27 | 5-methoxypyrid-3-yl | methoxy |
| 28 | 5-chloropyrid-3-yl | benzoyloxy |
| 29 | 6-chloropyridazin-3-yl | methoxy |
| 30 | 6-chloropyrazin-2-yl | methoxy |
| 31 | 5-bromopyrid-3-yl | methoxy |

Specific examples of compounds of formula (II) include those set out in Table II wherein the meanings of $R^1$ and $R^3$ are given.

| No. | $R^1$ | $R^3$ |
|---|---|---|
| 32 | 5-chloropyrid-3-yl | methyl |
| 33 | 5-chloropyrid-3-yl | benzyl |
| 34 | 5-chloropyrid-3-yl | 2,2-difluoroethyl |
| 35 | 5-chloropyrid-3-yl | 2-methylpropyl |

It will be appreciated that the bicyclic amine compounds of formula I are capable of existing in more than one isomeric form since the groups $R^1$ and $R^2$ may be positioned in either an exo or endo relationship, and the present invention embraces within its scope both exo and endo forms and mixtures thereof and also any further isomeric variants arising from cis and trans substitution patterns or chiral centres present in either of $R^1$ or $R^2$.

Suitable acid addition salts include those with an inorganic acid such as hydrochloric, hydrobromic, sulfuric, nitric and phosphoric acids, or an organic carboxylic acid such as oxalic, tartaric, lactic, butyric, toluic, hexanoic and phthalic acids, or sulphonic acids such as methane, benzene and toluene sulphonic acids.

The preparation of the compounds of formula (I) may be accomplished by use of one or more of the following synthetic techniques described below and further illustrated in the Examples.

The compounds of general formula (I) can be prepared from compounds of general formula (VI) by treatment with a suitable base, such as lithium diisopropylamide (LDA), followed by reaction with an aryl or heteroaryl halide ($R^1Hal$).

The compounds of general formula (VI) can be prepared by treating compounds of general formula (VIII) with an arene sulfonyl methyl isocyanide, such as tosylmethyl isocyanide, in the presence of a suitable base, such as potassium ethoxide.

Compounds of general formula (VIII) can be prepared by the Robinson tropinone synthesis, see, for instance, J. Chem. Soc., 1917, 111, 762. As an alternative compounds of general formula (VIII) can be prepared from cyclohepta-2, 6-dienone (XI) by reaction with an amine ($R^2NH_2$) in a similar manner to that described in, for instance, Tetrahedron, 1973, 155, Bull, Chem, Chem, Soc, Jpn., 1971, 44, 1708 and J. Org. Chem., 1971, 36, 1718.

In another process compounds of formula (I) where $R^2$ repesents the group $XR^3$ can be prepared from the corresponding compounds wherein $R^2$ is hydrogen, the preparation of which is disclosed in International Patent Application WO96/37494, by reaction with a peroxide such as dimethyldioxirane to give a compound of formula (I) wherein $R^2$ is hydroxy, which can then be reacted with compounds of $R^3$—L where is an easily displaceable atom or group such as a halogen atom or the mesylate or tosylate group. In a variation of this process the compound of formula (I) where $R^2$ is hydrogen can be reacted with a diacyl peroxide, such as benzoyl peroxide, and the resultant ester hydrolysed to yield the compound where $R^2$ is hydroxy.

Alternatively, compounds of general formula (I) can be prepared by treatment of a compound of general formula (IX) with an aryl- or heteroaryl-acetonitrile of general formula (X) in the presence of a suitable base, such as sodium hydride, as described in J. Med. Chem., 1975, 18, 496.

The following methods can be used to prepare compounds of formula I wherein $R^2$ represents an amino or substituted amino group.

N,N-Dialkylhydrazines can be reacted with cyclohepta-2,6-dienenone to give 8-dialkylamino-8-aza[3.2.1]octan-3-ones. These materials can then be transformed to the required products of formula (I) such as exo-3-(5-chloropyrid-3-yl)-endo-3-cyano-8-N',N'-dimethylamino-8-azabicyclo[3.2.1]octane, (1), by the procedure set out below.

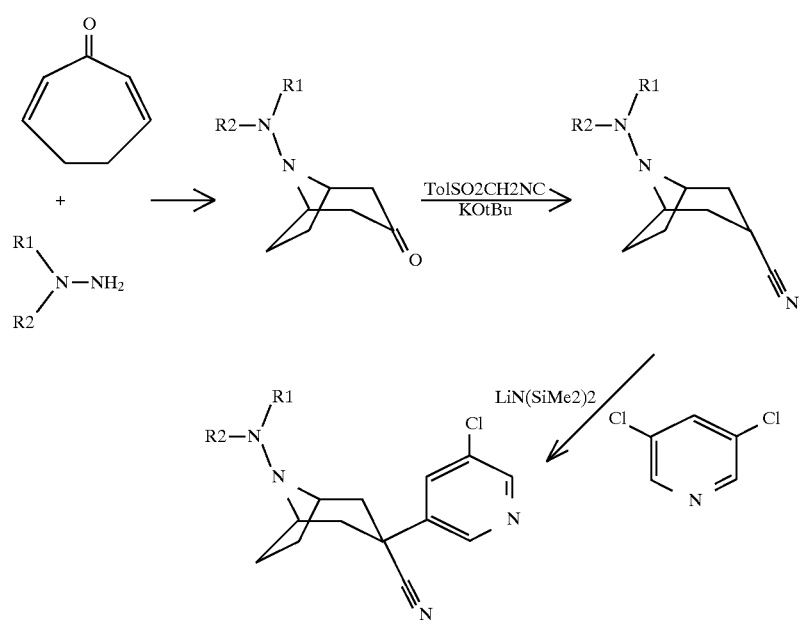

Another method uses the reaction of a compound of formula (I) where $R^2$ is hydrogen with a suitable aminating agent such O-2,4-dinitrophenylhydroxylamine as is illustrated by the reaction of, for example, exo-3-(5-chloropyrid-3-yl)-endo-3-cyano -8-azabicyclo[3.2.1]octane with this agent, in the presence of a suitable base, such as diisopropylethylamine, in a solvent, such as tetrahydrofuran, for several hours at 65° C.

In another method the compound of formula (I) wherein $R^2$ is hydrogen can be reacted with an N- t-butoxycarbonyl substituted oxiridazine to give the compound where $R^2$ is t-butoxycarbonylamino which can then be converted to the compound of formula (I) where R2 is amino (J Vidal, L Guy, S Sterin, A Collet *J. Org. Chem.,*58 (1993) 18, 4791 and J Vidal, S Damestoy, S Sterin, A Collet *Tetrahedron Lett.*, 36, (1995), 9, 1439). Thus, for example, exo-3-(5-chloropyrid-3-yl)-endo-3-cyano-8-azabicyclo[3.2.1]octane can be reacted with a t-butyloxycarbamoyl substituted phenyloxiradazine to give exo-3-(5-chloropyrid-3-yl)-endo-3-cyano-8-t-butyloxy-carbamoyl-8-azabicyclo[3.2.1]octane. This may be transformed with a suitable acid, such as trifluoroacetic acid, followed by a base, such as aqueous sodium hydroxide to give exo-3-(5-chloropyrid-3-yl)-endo-3-cyano-8-amino-8-azabicyclo[3.2.1]octane.

The amino group can thereafter be further derivatised, for example acylated or alkylated, to give other compounds of formula (I).

The N-oxides of formula (II) may be produced as by-products in certain of the procedures set out above. They may also be made specifically by the alkylation of the compounds of formula (I) where R2 is hydroxy in the presence of silver salts such as silver carbonate.

The compounds of general formula (VI) are believed not to have been previously described. Accordingly in a further aspect the invention provides compounds of formula (VI) wherein $R^2$ has any of the meanings given hereinabove.

In a further aspect the invention provides a method of combating insect and like pests at a locus by applying to the locus or the pests an insecticidally-effective amount of an insecticidal composition comprising the compounds of Formula I or an acid addition salt thereof.

The compounds of Formula I and acid addition salts thereof may be used to combat and control infestations of insect pests such as Lepidoptera, Diptera, Homoptera and Coleoptera (including Diabrotica i.e. corn rootworms) and also other invertebrate pests, for example, acarine pests. The insect and acarine pests which may be combated and controlled by the use of the invention compounds include those pests associated with agriculture (which term includes the growing of crops for food and fibre products), horticulture and animal husbandry, forestry, the storage of products of vegetable origin, such as fruit, grain and timber, and also those pests associated with the transmission of diseases of man and animals. Examples of insect and acarine pest species which may be controlled by the compounds of Formula I include:

*Myzus persicae* (aphid), *Aphis gossypii* (aphid), *Aphis fabae* (aphid), *Aedes aegypti* (mosquito), Anopheles spp. (mosquitos), Culex spp. (mosquitos), *Dysdercus fasciatus* (capsid), *Musca domestica* (housefly), *Pieris brassicae* (white butterfly), *Plutella xylostella* (diamond back moth), *Phaedon cochleariae* (mustard beetle), Aonidiella spp. (scale insects), Trialeurodes spp. (white flies), *Bemisia tabaci* (white fly), *Blattella germanica* (cockroach), *Periplaneta americana* (cockroach), *Blatta orientalis* (cockroach) *Spodoptera littoralis* (cotton leafworm), *Heliothis virescens* (tobacco budworm) *Chortiocetes terminifera* (locust), Diabrotica spp. (rootworms), Agrotis spp. (cutworms), *Chilo partellus* (maize stem borer), *Nilaparvata lugens* (planthopper), *Nephotettix cincticeps* (leafhopper), *Panonychus ulmi* (European red mite), *Panonychus citri* (citrus red mite), *Tetranychus urticae* (two-spotted spider mite), *Tetranychus cinnabarinus* (carmine spider mite), *Phyllcoptruta oleivora* (citrus rust mite), *Polyphagotarsonemus latus* (broad mite) and Brevipalpus spp. (mites).

In order to apply the compounds of Formula I to the locus of the nematode, insect or acarid pest, or to a plant susceptible to attack by the nematode, insect or acarid pest, the compound is usually formulated into a composition which includes in addition to the the compounds of Formula I suitable inert diluent or carrier materials, and/or surface active agents. The amount of composition generally applied for the control of nematode pests gives a rate of active ingredient from 0.01 to 10 kg per hectare, preferably from 0.1 to 6 kg per hectare.

The compositions can be applied to the soil, plant or seed, to the locus of the pests, or to the habitat of the pests, in the form of dusting powders, wettable powders, granules (slow or fast release), emulsion or suspension concentrates, liquid solutions, emulsions, seed dressings, fogging/smoke formulations or controlled release compositions, such as microencapsulated granules or suspensions.

Dusting powders are formulated by mixing the active ingredient with one or more finely divided solid carriers and/or diluents, for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers.

Granules are formed either by absorbing the active ingredient in a porous granular material for example pumice, attapulgite clays, fuller's earth, kieselguhr, diatomaceous earths, ground corn cobs, and the like, or on to hard core materials such as sands, silicates, mineral carbonates, sulphates, phosphates, or the like. Agents which are commonly used to aid in impregnation, binding or coating the solid carriers include aliphatic and aromatic petroleum solvents, alcohols, polyvinyl acetates, polyvinyl alcohols, ethers, ketones, esters, dextrins, sugars and vegetable oils with the active ingredient. Other additives may also be included, such as emulsifying agents. wetting agents or dispersing agents.

Microencapsulated formulations (microcapsule suspensions CS) or other controlled release formulations may also be used, particularly for slow release over a period of time, and for seed treatment.

Alternatively the compositions may be in the form of liquid preparations to be used as dips, irrigation additives or sprays, which are generally aqueous dispersions or emulsions of the active ingredient in the presence of one or more known wetting agents, dispersing agents or emulsifying agents (surface active agents). The compositions which are to be used in the form of aqueous dispersions or emulsions are generally supplied in the form of an emulsifiable concentrate (EC) or a suspension concentrate (SC) containing a high proportion of the active ingredient or ingredients. An EC is a homogeneous liquid composition, usually containing the active ingredient dissolved in a substantially non-volatile organic solvent. An SC is a fine particle size dispersion of solid active ingredient in water. To apply the concentrates they are diluted in water and are usually applied by means of a spray to the area to be treated.

Suitable liquid solvents for ECs include methyl ketone, methyl isobutyl ketone, cyclohexanone, xylenes, toluene, chlorobenzene, paraffins, kerosene, white oil, alcohols, (for example, butanol), methylnaphthalene, trimethylbenzene, trichloroethylene, N-methyl-2-pyrrolidone and tetrahydrofurfuryl alcohol (THFA).

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts of aliphatic monoesters of sulphuric acid, for example sodium lauryl sulphate, salts of sulphonated aromatic compounds, for example sodium dodecylbenzenesulphonate, sodium, calcium or ammonium lignosulphonate, or butylnaphthalene sulphonate, and a mixture of the sodium salts of diisopropyl- and triisopropylnaphthalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

These concentrates are often required to withstand storage for prolonged periods and after such storage, to be capable of dilution with water to form aqueous preparations which remain homogeneous for a sufficient time to enable them to be applied by conventional spray equipment. The concentrates may contain 10–85% by weight of the active ingredient or ingredients. When diluted to form aqueous preparations such preparations may contain varying amounts of the active ingredient depending upon the purpose for which they are to be used.

The compounds of Formula I may also be formulated as powders (dry seed treatment DS or water dispersible powder WS) or liquids (flowable concentrate FS, liquid seed treatment LS, or microcapsule suspension CS) for use in seed treatments.

In use the compositions are applied to the insect pests, to the locus of the pests, to the habitat of the pests, or to growing plants liable to infestation by the pests, by any of the known means of applying pesticidal compositions, for example, by dusting, spraying, or incorporation of granules.

The compound of Formula I may be the sole active ingredient of the composition or they may be admixed with one or more additional active ingredients such as insecticides, synergists, herbicides, fungicides or plant growth regulators where appropriate.

Suitable additional active ingredients for inclusion in admixture with a compound of Formula I may be compounds which will broaden the spectrum of activity of the compositions of the invention or increase their persistence in the location of the pest. They may synergise the activity of the compound of Formula I or complement the activity for example by increasing the speed of effect or overcoming repellency. Additionally multi-component mixtures of this type may help to overcome or prevent the development of resistance to individual components. The particular additional active ingredient included will depend upon the intended utility of the mixture and the type of complementary action required. Examples of suitable insecticides include the following:

a) Pyrethroids such as permethrin, esfenvalerate, deltamethrin, cyhalothrin in particular lambda-cyhalothrin, biphenthrin, fenpropathrin, cyfluthrin, tefluthrin, fish safe pyrethroids for example ethofenprox, natural pyrethrin, tetramethrin, s-bioallethrin, fenfluthrin, prallethrin and 5-benzyl-3-furylmethyl-(E)-(1R,3S)-2,2-dimethyl-3-(2-oxothiolan-3-ylidenemethyl) cyclopropane carboxylate;

b) Organophosphates such as profenofos, sulprofos, methyl parathion, azinphos-methyl, demeton-s-methyl, heptenophos, thiometon, fenamiphos, monocrotophos, profenophos, triazophos, methamidophos, dimethoate, phosphamidon, malathion, chloropyrifos, phosalone, terbufos, fensulfothion, fonofos, phorate, phoxim, pyrimiphos-methyl, pyrimiphos-ethyl, fenitrothion or diazinon;

c) Carbamates (including aryl carbamates) such as pirimicarb, cloethocarb, carbofuran, furathiocarb, ethiofencarb, aldicarb, thiofurox, carbosulfan, bendiocarb, fenobucarb, propoxur or oxamyl;

d) Benzoyl ureas such as triflumuron, or chlorfluazuron;

e) Organic tin compounds such as cyhexatin, fenbutatin oxide, azocyclotin;

f) Macrolides such as avermectins or milbemycins, for example such as abamectin, ivermectin, and milbemycin;

g) Hormones and pheromones;

h) Organochlorine compounds such as benzene hexachloride, DDT, chlordane or dieldrin;

i) Amidines, such as chlordimeform or amitraz;

j) Fumigant agents;

k) Imidacloprid.

In addition to the major chemical classes of insecticide listed above, other insecticides having particular targets may be employed in the mixture if appropriate for the intended utility of the mixture. For instance selective insecticides for particular crops, for example stemborer specific insecticides for use in rice such as cartap or buprofezin can be employed. Alternatively insecticides specific for particular insect species/stages for example ovo-larvicides such as chlofentezine, flubenzimine, hexythiazox and tetradifon, motilicides such as dicofol or propargite, acaricides such as bromopropylate, chlorobenzilate, or growth regulators such as hydramethylron, cyromazine, methoprene, chlorofluazuron and diflubenzuron may also be included in the compositions.

Examples of suitable synergists for use in the compositions include piperonyl butoxide, sesamax, safroxan and dodecyl imidazole.

Suitable herbicides, fungicides and plant-growth regulators for inclusion in the compositions will depend upon the intended target and the effect required.

An example of a rice selective herbicide which can be included is propanil, an example of a plant growth regulator for use in cotton is "Pix", and examples of fungicides for use in rice include blasticides such as blasticidin-S. The ratio of the compounds of Formula I to the other active ingredient in the composition will depend upon a number of factors including type of target, effect required from the mixture etc. However in general, the additional active ingredient of the composition will be applied at about the rate as it is usually employed, or at a slightly lower rate if synergism occurs.

The invention is illustrated by the following examples. Examples 1 to 10 illustrate the preparation of a range of compounds of formula (I).

Examples 11 to 17 illustrate formulations suitable for the application of the compounds of Formula I according to the invention. The following ingredients are referred to by their Registered Trade Marks and have the composition as shown below.

| Registered Trade Mark | Composition |
|---|---|
| Synperonic NP8 | Nonylphenol-ethylene oxide condensate |
| Synperonic NP13 | |
| Synperonic OP10 | |

-continued

| Registered Trade Mark | Composition |
|---|---|
| Aromasol H | Alkylbenzene solvent |
| Solvesso 200 | Inert organic diluent |
| Keltrol | Polysaccharide |

EXAMPLE 1

This example illustrates the preparation of exo-3-(5-chloropyrid-3-yl)-endo-3-cyano-8-methoxy-8-azabicyclo[3.2.1]octane.

N,N-Diisopropylethylamine (14.5 ml) was added dropwise to a stirred suspension of O-methylhydroxylamine hydrochloride (2.32 g) in isopropyl alcohol (25 ml). After 30 minutes cyclohepta-2,6-dienone (3.0 g) in isopropyl alcohol (5 ml) was added dropwise. After 24 hours N,N-diisopropylethylamine (4.9 ml) was added. After 6 hours the mixture was allowed to stand at room temperature overnight. The mixture was evaporated under reduced pressure, diethyl ether added and the resulting mixture extracted with 2M hydrochloric acid (x3). The combined aqueous fractions were washed with diethyl ether (x3), neutralised with sodium hydroxide and extracted with diethyl ether (x3). The combined extracts were washed with brine, dried (MgSO$_4$) and evaporated under reduced pressure. Kugelrohr distillation gave 8-methoxy-8-azabicyclo[3.2.1]octan-3-one (0.86 g). Tosylmethyl isocyanide (2.52 g) was added to a stirred suspension of potassium t-butoxide (2.17 g) in 1,2-dimethoxyethane (10 ml) at such a rate to keep the temperature below 10° C. After 45 minutes 8-methoxy-8-azabicyclo[3.2.1]octan-3-one (1.0 g) in 1,2-dimethoxyethane (10 ml) was added dropwise. After 30 minutes the mixture was allowed to warm to room temperature. After 4 hours the mixture was allowed to stand at room temperature overnight and water was then added. The resulting mixture was extracted with ethyl acetate (x3) and the combined extracts washed with brine, dried (MgSO$_4$) and evaporated under reduced pressure. Chromatography [SiO$_2$; hexane:ethyl acetate (90:10)] gave exo-3-cyano-8-methoxy-8-azabicyclo[3.2.1]octane (0.40 g). Lithium bis(trimethylsilyl)amide (2.42 ml of a 1M solution in tetrahydrofuran) was added dropwise to a stirred solution of exo-3-cyano-8-methoxy-8-azabicyclo[3.2.1]octane (0.40 g) and 3,5-dichloropyridine (0.358 g) in tetrahydrofuran (5 ml) at 0° C. After 1 hour the mixture was allowed to warm to room temperature. After 5 hours water was added and the mixture extracted with ethyl acetate (x3). The combined extracts were washed with brine, dried (MgSO$_4$) and evaporated under reduced pressure. Preparative thin layer chromatography [SiO$_2$; ethyl acetate] gave exo-3-(5-chloropyrid-3-yl)-endo-3-cyano-8-methoxy-8-azabicyclo[3.2.1]octane (0.192 g) m.p. 107.5°–108.5° C.

EXAMPLE 2

This Example illustrates the preparation of exo-3-(5-chloropyrid-3-yl)-endo-3-cyano-8-benzoyloxy-8-azabicyclo[3.2.1]octane.

exo-3-(5-Chloropyrid-3-yl)-endo-3-cyano-8-azabicyclo[3.2.1]octane (Reference 1) (2.00 g) was added to a suspension of disodium hydrogen phosphate (5.74 g) in tetrahydrofuran (20 ml). The mixture was stirred at ambient temperature and a solution of dibenzoyl peroxide (3.07 g, 70% stabilised with water) in tetrahydrofuran (30 ml) was added dropwise over 15 minutes. The mixture was stirred for 24 h, treated with sodium metabisulfite and partioned between saturated aqueous sodium carbonate and ethyl acetate. The organic fraction was separated, the aqueous fraction extracted a further three times with ethyl acetate and the combined organic fractions dried (magnesium sulfate) and evaporated under reduced pressure to give an off-white solid, 3.89 g. The solid was fractionated by chromatography (silica, 10%–30% ethyl acetate/hexane) to give the required product as a colourless solid, 2.56 g. mp 153°–5° C.
$^1$H NMR (CDCl$_3$) 2.25–2.80(8H,m); 4.00–4.20(2H,broad m); 7.40–7.50(2H,m); 7.55–7.65(1H,m); 7.85(1H,t); 7.90–8.10(2H,m); 8.55(1H,s); 8.75(1H,d).

EXAMPLE 3

This Example illustrates the preparation of exo-3-(5-chloropyrid-3-yl)-endo-3-cyano-8-hydroxy-8-azabicyclo[3.2.1]octane.

The product from Example 2 (2.58 g) was added in portions over 15 minutes to a solution of potassium hydroxide (0.59 g) in methanol (50 ml) with stirring at ambient temperature under an atmosphere of nitrogen. The resulting suspension was stirred for 2 h to give a yellow solution and stored for 18 h. The methanol was evaporated under reduced pressure and the residue partioned between ethyl acetate and water (10 ml). The organic fraction was separated, the aqueous fraction re-extracted three times with ethyl acetate, the combined organic fractions dried (magnesium sulfate) and evaporated under reduced pressure to give a colourless solid, 1.99 g. The solid was extracted with hot hexane (3×100 ml), the insoluble solid was filtered from solution and dried under vacuum to give the required product as a colourless solid, 1.71 g.

EXAMPLE 4

This Example illustrates the preparation of exo-3-(5-chloropyrid-3-yl)-endo-3-cyano-8-hydroxy-8-azabicyclo[3.2.1]octane.

exo-3-(5-Chloropyrid-3-yl)-endo-3-cyano-8-azabicyclo[3.2.1]octane (Reference 1) (0.10 g) in acetone (1 ml) was cooled to 0° C. with stirring and a solution of dimethyl dioxirane [Reference 2] (10.6 ml of 0.038M solution in acetone) added in one portion. The pale pink mixture was stirred at 0° C. for 15 minutes and evaporated under reduced pressure to give a yellow solid. The solid was dissolved in ethyl acetate, dried (magnesium sulfate) and re-evaporated under reduced pressure to give a yellow solid, 0.090 g. The solid was fractionated by preparative thick layer chromatography (silica, eluted with ethyl acetate) to give the required product, 0.025 g as a colourless solid. Mp 133.5°–135.5° C., molecular ion 263.
$^1$H NMR (CDCl$_3$) indicated a mixture of axial and equatorial N-hydroxy isomers, ratio 2:5. 1.80–2.20(1H,broad signal); 1.90(d) and 2.10(m) (total 3H); 2.35(m) and 2.85 (dd) total 5H; 3.60(broad signal) and 3.75(broad signal) total 2H; 7.85(t)and 7.95(t) total 1H; 8.52(1H,m); 8.70(d) and 8.80(d) total 1H.

EXAMPLE 5

This Examples illustrates the preparation of exo-3-(5-chloropyrid-3-yl)-endo-3-cyano-8-(2,2-difluoroethoxy)-8- azabicyclo[3.2.1]octane and exo-3-(5-chloropyrid-3-yl)-endo-3-cyano-8-(2,2-difluoroethyl)-8-azabicyclo[3.2.1]octane-N-oxide.

Sodium hydride (60% dispersion in mineral oil, 0.030 g) in dry N,N-dimethylformamide (1 ml) was stirred at ambient temperature and a solution of the product from Stage Two (0.20 g) in dry N,N-dimethylformamide (3 ml) added dropwise. The yellow solution was stirred for 0.5 h, cooled to −10° C. and 2-bromo-1,1-difluoroethane (0.11 g) in dry N,N-dimethylformamide added. The reaction was stirred at 0° C. for 5 h and stored at −10° C. for 18 h. The reaction was allowed to warm to ambient temperature, poured into water (5 ml), extracted three times with ethyl acetate, the combined organic fractions washed twice with saturated aqueous sodium chloride solution and dried (magnesium sulfate). The solvent was evaporated under reduced pressure to give a yellow oil which was fractionated by preparative thick layer chromatography (silica, eluted with 50% ethyl acetate in hexane) to give exo-3-(5-chloropyrid-3-yl)-endo-3-cyano-8-(2,2-difluoroethoxy)-8-azabicyclo[3.2.1]octane (0.025 g) as a colourless solid, mp 112°–4° C. $^1$H NMR (CDCl$_3$) 1.90–2.70(8H,m); 3.70 and 3.80(2H,m)3.80–4.00 (2H,m); 5.80–6.20(1H,tt); 7.80 and 7.90(1H,two t); 8.55 (1H,d); 8.65 and 8.75(1H,two d) as a mixture of axial and equatorial isomers, ratio 1:4; and exo-3-(5-chloropyrid-3-yl)-endo-3-cyano-8-(2,2-difluoroethyl)-8-azabicyclo[3.2.1]octane-N-oxide, 0.048 g, as a colourless solid, mp 171°–3° C. $^1$H NMR(CDCl$_3$) 2.20(2H,d); 2.35(2H,m); 2.80(2H,m); 3.55(2H,dd); 3.65–3.85(4H,m); 6.60–7.00(1H,tt); 8.18(1H, t); 8.60(1H,d); 8.90(1H,d).

Reference 1 Zeneca Ltd. WO96/37494, 13th May 1996.

Reference 2 R W Murray and R Jeyarawan *J. Org Chem.* 50 2847 (1985)

EXAMPLE 6

The following were prepared using a similar procedure from exo-3-(5-chloropyrid-3-yl)-endo-3-cyano-8-hydroxy-8-azabicyclo[3.2.1]octane and the appropriate hydrocarbyl bromide:

(a) exo-3-(5-Chloropyrid-3-yl)-endo-3-cyano-8-(benzyloxy)-8-azabicyclo[3.2.1]octane, colourless solid, mp 66°–8° C.

$^1$H NMR (CDCl$_3$) consistent with a mixture of axial and equatorial N-benzyloxy isomers, ratio 3:7; 1.90(dd), 2.20–2.40(m) 2.65–2.75(dd) total 8H; 3.60(broad m) and 3.75(broad m) total 2H; 4.70(s) and 4.80(s) total 2H; 7.25–7.40(5H,m); 7.80(t) and 7.88(t) total 1H; 8.52(1H,two d) 8.65(d) and 8.75(d) total 1H.

(b) exo-3-(5-Chloropyrid-3-yl)-endo-3-cyano-8-(allyloxy)-8-azabicyclo[3.2.1]octane, colourless solid, mp 51°–3° C.

$^1$H NMR (CDCl$_3$) consistent with a mixture of axial and equatorial N-allyloxy isomers, ratio 3:7; 1.90–2.80(8H,m); 3.70 and 3.80(2H,m); 4.20 and 4.30(2H,two dd); 5.15–5.40 (2H,m); 5.85–6.10(1H,m); 7.80 and 7.90(1H,two t); 8.55 (1H,d); 8.65 and 8.80(1H,two d).

(c) exo-3-(5-Chloropyrid-3-yl)-endo-3-cyano-8-(2-methylpropyloxy)-8-azabicyclo[3.2.1]octane, yellow oil, $^1$H NMR (CDCl$_3$) consistent with a mixture of axial and equatorial N-alkoxy isomers, ratio 1:2; 0.90 and 0.95(6h,two d); 1.80–2.10(2H,m); 2.20–2.35(4H,m); 2.38(2H,d); 2.68 and 2.75(two d) total 1H; 3.45 and 3.55(two d) total 2H; 3.68 and 3.75(broad m) total 2H; 7.80 and 7.95(two t) total 1H; 8.55(1H,d); 8.68 and 8.78(two d) total 1H.

(d) exo-3-(5-Chloropyrid-3-yl)-endo-3-cyano-8-(2-methylpropyl)-8-azabicyclo[3.2.1]octane-N-oxide, yellow gum, $^1$H NMR (CDCl$_3$) 1.18(6H,d); 2.15–2.20(1H,m); 2.25–2.38 (3H,m); 2.48–2.62(1H,m); 2.70–2.80(2H,m) 3.25(2H,d); 3.50 and 3.58(2H,dd); 3.70(2H,broad m); 8.25(1H,t); 8.55 (1H,d); 8.95(1H,d).

EXAMPLE 7

Preparation of and exo-3-(5-chloropyrid-3-yl)-endo-3-cyano-8-(benzyl)-8-azabicyclo[3.2.1]octane-N-oxide.

exo-3-(5-Chloropyrid-3-yl)-endo-3-cyano-8-hydroxy-8-azabicyclo[3.2.1]octane (0.50 g) in dry toluene (1 ml) was treated with silver carbonate (0.052 g) and benzyl bromide (0.025 ml) added. The reaction mixture was stirred under an atmosphere of nitrogen and heated to reflux for 2.5 h. The mixture was cooled to ambient temperature, filtered, the insolubles washed with dichloromethane and the combined filtrate evaporated under reduced pressure to give a yellow oil. The oil was fractionated by preparative thick layer chromatography (silica, 50% ethyl acetate in hexane) to give the required product as an orange gum, 0.028 g. $^1$H NMR (CDCl$_3$) consistent with a mixture of axial and equatorial N-benzyl oxide isomers, 2.10–2.35(2H,m); 2.50(2H,m); 2.85(2H,m); 3.50(2H,dd); 3.60–3.80(2H,broad m)4.45(2H, s)7.45(3H,m); 7.60(2H,m); 7.85 and 8.20(1H,two t); 8.55 (1H,d); 8.70 and 8.90 (1H,two d).

EXAMPLE 8

The following example illustrates the preparation of exo-3-(5-chloropyrid-3-yl)-endo-3-cyano-8-acetoxy-8-azabicyclo[3.2.1]octane.

A suspension of sodium hydride (0.015 g, 60% dispersion in mineral oil) in dry N,N-dimethylformamide (1 ml) was stirred at −10° C. under an atmosphere of nitrogen and a solution of exo-3-(5-chloropyrid-3-yl)-endo-3-cyano-8-hydroxy-8-azabicyclo[3.2.1]octane (0.100 g) in dry N,N-dimethylformamide (1 ml) was added dropwise. The reaction was stirred for 0.75 h, acetyl chloride (0.027 ml) added and the mixture stirred at 0° C. for 3 h and stored at −10° C. for 18 h. The mixture was treated with water and extracted three times with ethyl acetate. The organic fractions were combined, washed twicewith saturated sodium chloride solution, dried ( magnesium sulfate) and evaporated under reduced pressure to give an oil. The oil was fractionated by preparative thick layer chromatography to give the required product as a colourless solid, 0.055 g, mp 141°–2° C.

$^1$H NMR (CDCl$_3$) 2.05(3H,s); 2.20–2.65(8H,m); 3.85–4.00 (2H,m); 7.80 and 7.90(two t) total 1H; 8.55(1H,d); 8.70(1H, d).

EXAMPLE 9

This Example illustrates the preparation of exo-3-(5-chloropyrid-3-yl)-endo-3-cyano-8-t-butoxycarbonylamino-8-azabicyclo[3.2.1]octane.

exo-3-(5-Chloropyrid-3-yl)-endo-3-cyano-8-azabicyclo [3.2.1]octane (1.0 g) was dissolved in tertiary butyl methyl ether at ambient temperature with stirring under an atmosphere of nitrogen and tertiary butoxycarbonyl-3-(4-cyanophenyl)-oxiziridine (1.0 g) was added. The solution was stirred for 2 h and stored for 18 h. The colourless solid, which had precipitated, was filtered from solution, washed with diethyl ether and dried under vacuum to give exo-3-(5-chloropyrid-3-yl)-endo-3-cyano-8-t-butoxycarbonylamino-8-azabicyclo[3.2.1]octane, 0.96 g, mp 183°–5° C.

$^1$H NMR (CDCl$_3$) 1.45(9H,s); 2.10–2.20(2H,m); 2.30–2.40 (2H,dd); 2.45–2.60(4H,m); 3.58(2H,broad m); 5.65(1H,s); 7.75(1H,t); 8.55(1H,d); 8.72(1H,d).

EXAMPLE 10

This Example illustrates the preparation of exo-3-(5-chloropyrid-3-yl)-endo-3-cyano-8-amino-8-azabicyclo[3.2.1]octane as the di-hydrochloride salt thereof.

exo-3-(5-chloropyrid-3-yl)-endo-3-cyano-8-t-butoxycarbonylamino-8-azabicyclo[3.2.1]octane (0.10 g) was treated with aqueous hydrochloric acid (1.0 ml, 4M.) and stirred at ambient temperature for 2 h. The solution was evaporated under reduced pressure, toluene added to the residue and re-evaporated to give the di-hydrochloride salt of the required product, exo-3-(5-chloropyrid-3-yl)-endo-3-cyano-8-amino-8-azabicyclo[3.2.1]octane, as a colourless solid, 0.050 g.

$^1$H NMR (deuterated DMSO) 2.25–2.40(4H,broad signal); 2.45–2.75(4H,m); 3.95(2H,broad signal); 8.25(1H,broad signal); 8.68(1H,d); 8.80(1H,d), remaining hydrogens exchanged with residual water in NMR solvent, broad signal at 5.0.

EXAMPLE 11

This Example illustrates an emulsifiable concentrate composition which is readily convertible by dilution with water into a liquid preparation suitable for spraying purposes. The concentrate has the following composition:

|  | % Weight |
| --- | --- |
| Compound No. 1 | 25.5 |
| SYNPERONIC NP13 | 2.5 |
| Calcium dodecylbenzenenesulphonate | 2.5 |
| AROMASOL H | 70 |

EXAMPLE 12

This Example illustrates a wettable powder composition which is readily convertible by dilution with water into a liquid preparation suitable for spraying purposes. The wettable powder has the following composition:

|  | % Weight |
| --- | --- |
| Compound No. 13 | 25.0 |
| Silica | 25.0 |
| Sodium lignosulphonate | 5.0 |
| Sodium lauryl sulphate | 2.0 |
| Kaolinite | 43.0 |

EXAMPLE 13

This Example illustrates a dusting powder which may be applied directly to plants or other surfaces and comprises 1% by weight of Compound No. 25 and 99% by weight of talc.

EXAMPLE 14

This Example illustrates a concentrated liquid formulation suitable for application by ultra low volume techniques after mixing with paraffinic diluents.

|  | % Weight |
| --- | --- |
| Compound No. 29 | 90.0 |
| SOLVESSO 200 | 10.0 |

EXAMPLE 15

This Example illustrates a capsule suspension concentrate which is readily convertible by dilution with water to form a preparation suitable for application as an aqueous spray.

|  | % Weight |
| --- | --- |
| Compound No. 45 | 10.0 |
| Alkylbenzene solvent (e.g. AROMASOL H) | 5.0 |
| Toluene di-isocyanate | 3.0 |
| Ethylenediamine | 2.0 |
| Polyvinyl alcohol | 2.0 |
| Bentonite | 1.5 |
| Polysaccharide (e.g. KELTROL) | 0.1 |
| Water | 76.4 |

EXAMPLE 16

A ready for use granular formulation:

|  | % Weight |
| --- | --- |
| Compound No. 4 | 0.5 |
| SOLVESSO 200 | 0.2 |
| nonylphenol ethoxylate (eg Synperonic NP8) | 0.1 |
| Calcium carbonate granules (0.3–0.7 mm) | 99.2 |

EXAMPLE 17

An aqueous suspension concentrate:

|  | % Weight |
| --- | --- |
| Compound No. 8 | 5.0 |
| Kaolinite | 15.0 |
| Sodium lignosulphonate | 3.0 |
| nonylphenolethoxylate (eg Synperonic NP 8) | 1.5 |
| propylene glycol | 10.0 |
| Bentonite | 2.0 |
| Polysaccharide (eg Keltrol) | 0.1 |
| Bactericide (eg Proxel; Proxel is a registered Trade Mark) | 0.1 |
| Water | 63.3 |

EXAMPLE 18

This Example illustrates a water dispersible granule formulation.

|  | % Weight |
| --- | --- |
| Compound No. 20 | 5 |
| Silica | 5 |
| Sodium lignosulphate | 10 |
| Sodium dioctylsulphosuccinate | 5 |
| Sodium acetate | 10 |
| Montmorillonite powder | 65 |

EXAMPLE 19

This Example illustrates the insecticidal properties of the compounds of Formula I. The activity of the the compounds of Formula I was determined using a variety of pests. The pests were treated with a liquid composition containing 500 parts per million (ppm) by weight of the compound unless otherwise stated. The compositions were made by dissolving the compound in acetone and ethanol (50:50) mixture and diluting the solutions with water containing 0.05% by weight of a wetting agent sold under the trade name "SYN-PERONIC" NP8 until the liquid composition contained the required concentration of the compound. "SYNPERONIC" is a Registered Trade Mark.

The test procedure adopted with regard to each pest was basically the same and comprised supporting a number of the pests on a medium which was usually a substrate, a host plant or a foodstuff on which the pests feed, and treating either or both the medium and the pests with the compositions. The mortality of the pests was then assessed at periods usually varying from two to five days after the treatment.

The results of the tests against peach aphid (*Myzus persicae*) are given below. The results indicate a grading of mortality (score) designated as A, B or C wherein C indicates less than 40% mortality, B indicates 40–79% mortality and A indicates 80–100% mortality; "–" indicates that either the compound was not tested or no meaningful result was obtained. In this test Chinese cabbage leaves were infested with aphids, the infested leaves were sprayed with the test composition, and the mortality assessed after 3 days.

In this test Compounds nos. 1, 6, 16, 20, 23, 25, 32, 33, 34 and 35 of Table 1 gave a grading of A.

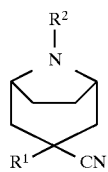
(I)

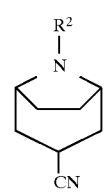
(VI)

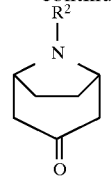
(VIII)

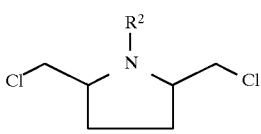
(IX)

$R^1 - CH_2 - CN$ (X)

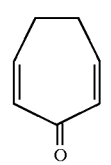
(XI)

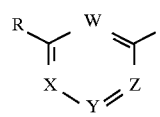
(A)

We claim:
1. A compound of formula (I) or formula (II)

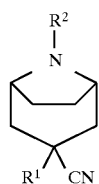
(I)

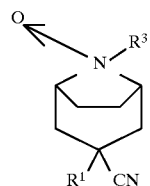
(II)

wherein $R^1$ represents a group of formula (A)

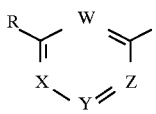
(A)

where each of W, X, Y and Z represents either a group CR or the nitrogen atom, provided that not more than two of W, X, Y, and Z represent the nitrogen atom and where each R present is independently selected from hydrogen and halogen atoms and cyano, amino, hydrazino, acylamino, hydroxy, alkyl, hydroxyalkyl, alkoxy, haloalkyl, haloalkoxy, alkenyl, alkenyloxy, alkoxyalkenyl, alkynyl, carboxylic acyl, alkoxycarbonyl, aryl and heterocyclyl groups, said groups having up to 6 carbon atoms, and wherein $R^2$ represents a group $XR^3$ where X represents oxygen or a group $NR^4$ where $R^3$ and $R^4$ are individually selected from hydrogen or a group selected from alkyl aryl, heteroaryl, aralkyl, heteroarylalkyl, alkenyl, aralkenyl, alkynyl, heterocyclylalkyl, alkoxycarbonyl, and carboxylic acyl groups, said groups having from 1 to 15 carbon atoms, said groups being unsubstituted or substituted by one or more substituents selected from halogen, cyano, carboxyl, carboxylic acyl, carbamyl, alkoxycarbonyl, alkoxy, alkylenedioxy, hydroxy, nitro, haloalkyl and alkyl groups; or an acid addition salt quaternary ammonium salt or N-oxide derived therefrom.

2. A compound according to claim 1 wherein $R^1$ represents a halo-substituted phenyl, pyridyl or diazinyl group.

3. A compound according to claim 1 where $R^1$ represents a phenyl or halophenyl group or a pyridyl, halopyridyl pyridazinyl, halopyridazinyl pyrazinyl, or halopyrazinyl group and X represents oxygen and $R^3$ represents hydrogen or a $C_{1-6}$ alkyl, alkenyl, alkynyl, phenyl, benzyl, acetyl or benzoyl group which is unsubstituted or substituted with one or more alkyl, alkoxy, alkoxycarbonyl or cyano groups or halogen atoms; or an acid addition salt thereof.

4. A compound according to claim 1 wherein $R^1$ is a halo-substituted pyridyl group X is oxygen and $R^3$ is a $C_{1-6}$ alkyl group.

5. An insecticidal or acaricidal or nematicidal composition comprising an insecticidally, acaricidally or nematicidally effective amount of a compound according to claim 1.

6. A method of combating and controlling insect acerine or nematode pests at a locus which comprises treating the pests or the locus of the pests with a nesticidally effective amount of a composition according to claim 5.

7. A method according to claim 6 wherein the pests are insect pests of growing plants.

8. A process of preparing a compound of formula (I) which comprises reacting a compound of formula (VI):

with a compound of formula $R^1Hal$ where Hal is a halide in the presence of a base.

* * * * *

UNITED STATES PATENT AND TRADEMARK OFFICE
CERTIFICATE OF CORRECTION

PATENT NO. : 5,859,024
DATED : January 12, 1999
INVENTOR(S) : Matthew Brian HOTSON et al.

It is certified that error appears in the above-identified patent and that said Letters Patent is hereby corrected as shown below:

On the title page, item [22] :

After "[22] Filed:" delete "May 31, 1997", and insert --May 13, 1997--.

Signed and Sealed this

First Day of June, 1999

*Attest:*

Q. TODD DICKINSON

*Attesting Officer*  *Acting Commissioner of Patents and Trademarks*